US008034837B2

(12) United States Patent
Albrecht et al.

(10) Patent No.: US 8,034,837 B2
(45) Date of Patent: Oct. 11, 2011

(54) POLYMORPHIC FORM OF 6-(4-CHLOROPHENYL)-2,2-DIMETHYL-7-PHENYL-2,3-DIHYDRO-1H-PYRROLIZIN-5-YLACETIC ACID

(75) Inventors: Wolfgang Albrecht, Ulm (DE); Thomas Kammermeier, Ulm (DE); Hans-Gunter Striegel, Blaubeuren (DE); Philipp Merckle, Blaubeuren-Weiler (DE); Stefan Laufer, Tübingen (DE)

(73) Assignee: Merckle GmbH, Ulm (DE)

( * ) Notice: Subject to any disclaimer, the term of this patent is extended or adjusted under 35 U.S.C. 154(b) by 561 days.

(21) Appl. No.: 11/886,933

(22) PCT Filed: Mar. 20, 2006

(86) PCT No.: PCT/EP2006/002539
§ 371 (c)(1),
(2), (4) Date: Jan. 15, 2009

(87) PCT Pub. No.: WO2006/100019
PCT Pub. Date: Sep. 28, 2006

(65) Prior Publication Data
US 2009/0209610 A1 Aug. 20, 2009

(30) Foreign Application Priority Data

Mar. 21, 2005 (DE) .................. 10 2005 012 971

(51) Int. Cl.
*A61K 31/407* (2006.01)
*C07D 209/52* (2006.01)
(52) U.S. Cl. ......... 514/413; 548/452; 548/516; 514/412
(58) Field of Classification Search .................. 548/452, 548/516; 514/412, 413
See application file for complete search history.

(56) References Cited

U.S. PATENT DOCUMENTS

| 5,260,451 A | 11/1993 | Dannhardt et al. |
| 5,939,415 A | 8/1999 | Laufer et al. |
| 5,942,535 A | 8/1999 | Laufer et al. |
| 5,958,943 A | 9/1999 | Laufer et al. |
| 7,078,535 B2 | 7/2006 | Dannhardt et al. |
| 7,132,441 B2 * | 11/2006 | Gregory et al. ............... 514/406 |
| 7,595,342 B2 * | 9/2009 | Hansen et al. ............... 514/574 |
| 2002/0028953 A1 | 3/2002 | Kammermeier et al. |

FOREIGN PATENT DOCUMENTS

| EP | 0 397 175 | 11/1990 |
| WO | WO-95/32970 | 12/1995 |
| WO | WO-95/32971 | 12/1995 |
| WO | WO-95/32972 | 12/1995 |
| WO | WO-01/55149 | 8/2001 |

OTHER PUBLICATIONS

Cossy et al., "Synthesis of ML-3000, an Inhibitor of Cyclooxygenase and 5-Lipoxygenase", J.Org.Chem. 1997, 62, 7900-7901.
Cossy et al., "Synthetic Studies Towards ML-3000 A Concise Synthesis of This Non-Steroidal Anti-Inflammatory Drug", Tetrahedron 1999, 55, 5145-5156.
Curten, Beate, "New Ways for the preparation of substituted pyrrolizines", Thesis, University Ulm 1998.
Dannhardt et al., "C-5 Functionalized 6,7-Diphenyl-2,3-dihydro-1H-pyrrolizines as Inhibitors of Bovine Cyclooxygenase and 5-Lipoxygenase", Arch.Pharma. 1994, 327, 509-514.
Kiefer, Werner, "Functionalized 6,7-diaryl-2,3-dihydro-1H-pyrrolizines", Thesis, University of Frankfurt on Main, 1992.
Laufer et al.,"(6,7-Diaryldihydropyrrolizin-5-yl)acetic Acids, a Novel Class of Potent Dual Inhibitors of Both Cyclooxygenase and 5-Liproxygenase", J.Med.Chem. 1994, 37, 1894-1897.
Rabasseda et al., "Antiinflammatory Cyclooxygenase and 5-Lipoxygenase Inhibitor", Drugs of the Future 1995, 20(10), 1007-1009.
Dannhardt et al., "Synthesis and Properties of 2,3-Dihydro-1H-pyrrolizines", Arch.Pharm. 1979, 312, 896-907.
Dannhardt et al., "Antiinflammatory 2,3-Dihydro-1H-pyrrolizines, XIII: Isomeric (Diaryl-dihydropyrroliinyl)acetic Acids and 2-(Diaryldihyropyrrolizinyl)-ethanols", Arch.Pharm. 1988, 321, 159-162.
Laufer et al., "Synthesis and Evaluation of a Novel Series of Pyrrolizine Derivatives as Dual Cyclooxygenase-1 and 5-Liproxygenase Inhibitors", Arch.Pharm. Pharm.Med.Chem. 1997, 330, 307-312.

* cited by examiner

*Primary Examiner* — Golam M Shameem
(74) *Attorney, Agent, or Firm* — Edwards Angell Palmer & Dodge LLP; Jeffrey D. Hsi; Mark D. Russett

(57) ABSTRACT

The present invention relates to a new crystalline modification of 6-(4-chlorophenyl)-2,2-dimethyl-7-phenyl-2,S-dihydro-1H-pyrrolizin-S-ylacetic acid which is referred to as polymorph B. It has a peak in the solid state $^{13}$C-NMR spectrum (with adamantane as external reference standard; CH group d=29.45 ppm) in the range from 179.8 to 180.2 ppm and can be processed directly to a pharmaceutical formulation.

7 Claims, 3 Drawing Sheets

POLYMORPHIC FORM OF 6-(4-CHLOROPHENYL)-2,2-DIMETHYL-7-PHENYL-2,3-DIHYDRO-1H-PYRROLIZIN-5-YLACETIC ACID

DESCRIPTION OF THE INVENTION

The present invention relates to a new polymorphic form of 6-(4-chlorophenyl)-2,2-dimethyl-7-phenyl-2,3-dihydro-1H-pyrrolizin-5-ylacetic acid (ML 3000) which is referred to as polymorph B, and to a process for its preparation.

ML 3000 (INN designation: licofelone) is a promising inhibitor of cylcooxygenase and 5-lipoxygenase which is suitable for the treatment of rheumatoid diseases and for the preventive treatment of allergy-induced disorders, concerning which see, for example, *Drugs of the Future* 1995, 20 (10):1007-1009. A possible preparation route is also to be found in this publication. Further possible preparations are described in EP-A-397175, WO 95/32970, WO 95/32971, WO 95/32972, WO 03/018583, *Archiv der Pharmazie* 312, 896-907 (1979); and 321, 159-162 (1988), *J. Med. Chem.* 1994 (37), 1894-1897, *Arch. Pharm. Pharm. Med. Chem.* 330, 307-312 (1997). In all these syntheses, the basic pyrrolizine structure is assembled by the method depicted in the formula diagram:

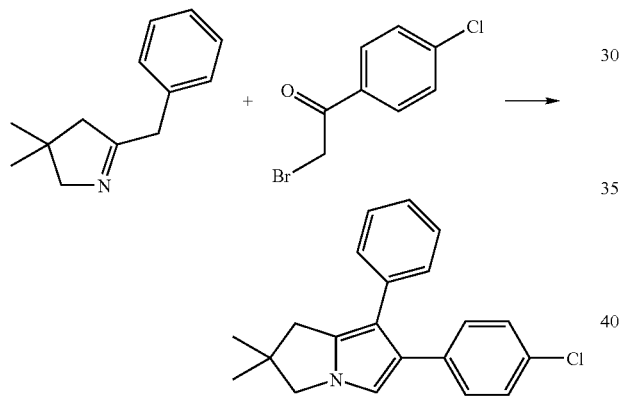

The introduction of the acetic acid residue in position 5 then takes place by reaction with diazoacetic ester or oxalic ester chloride and subsequent hydrolysis and reduction of the keto group using hydrazine.

WO95/32970, WO 95/32971 and WO 95/32972 describe the introduction of the acetic acid residue into compounds structurally related to ML-3000 by reacting these pyrrolizine compounds with oxalyl chloride or ethyl oxalyl chloride. For the industrial production of ML 3000, the introduction of the acetic acid residue with oxalyl chloride is preferred, as described in *Arch. Pharm.* 312, 896-907 (1979), WO 95/32970, WO 85/32971 and WO 95/32972. This is followed by reduction with hydrazine and potassium hydroxide (Huang Minlon variant of the Wolff-Kishner reduction).

WO 01/55149 also describes the introduction of the acetic acid residue with the aid of oxalyl chloride and subsequent reduction with hydrazine and potassium hydroxide. After the reaction is complete, and a 3-phase system is generated by adding an ether which is immiscible or has only limited miscibility with water, with the ML 3000 being present in the middle phase. Acidification of the middle phase results in a crystal modification which is referred to as polymorph A. Polymorph A has the advantage over the ML 3000 obtained according to the abovementioned prior art of greater stability and purity. However, polymorph A is still unsatisfactory in relation to the bulk and flow properties and the processibility to a pharmaceutical formulation. The crystals of polymorph A normally show a wide variation in particle size in the region of several hundred micrometers. In order to obtain an active pharmaceutical ingredient with uniform dissolution and absorption properties it is necessary to homogenize the resulting product batches differing in particle size by micronization. This signifies additional technical complexity, which is additionally associated with the disadvantage that the product after the micronization has a strong electrostatic charge which considerably impedes further processing.

The present invention is therefore based on the object of providing a further modification of ML 3000 which is improved in relation to the bulk and flow properties, and the processibility.

It has now surprisingly been found that this object is achieved by a new modification of ML 3000, which is referred to as polymorph B.

The present invention therefore relates to the polymorphic form B of 6-(4-chlorophenyl)-2,2-dimethyl-7-phenyl-2,3-dihydro-1H-pyrrolizin-5-ylacetic acid of the formula I

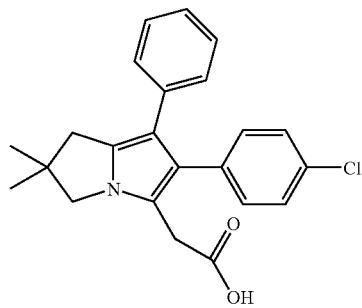

BRIEF DESCRIPTION OF THE FIGURES

These show
FIG. 1a the powder diffractogram of polymorph A
FIG. 1b an enlarged version of FIG. 1a
FIG. 2a the powder diffractogram of polymorph B
FIG. 2b an enlarged version of FIG. 2a
FIG. 3 the solid state $^{13}$C-NMR spectrum of polymorph B
FIG. 4 the solid state $^{13}$C-NMR spectrum of polymorph A The solid state $^{13}$C-NMR spectra were recorded in a Bruker AV-600 spectrometer at a proton frequency of 600 MHz and a C13-carbon frequency of 150 MHz. The spectra were recorded using the magic-angle spinning (MAS) technique and with a spinning rate of 15 kHz, without suppression of spinning side bands. Signal amplification is achieved by the linearly ramped cross polarization (CP) technique with a contact time of 1 ms. A two-pulse phase modulation (TPPM) decoupling was applied in the data acquisition. 1024 individual FIDs were accumulated for the spectrum of polymorph A, and 2048 FIDs for that of polymorph B. In both cases, a delay time of 3 s between the pulses and a spectral width of 50 kHz was chosen. Adamantane (CH group at 29.45 ppm) was employed as external shift reference standard.

Polymorph B is characterized by a peak in the solid state $^{13}$C-NMR spectrum in the range from 179.8 to 180.2 ppm.

Figure 1A:
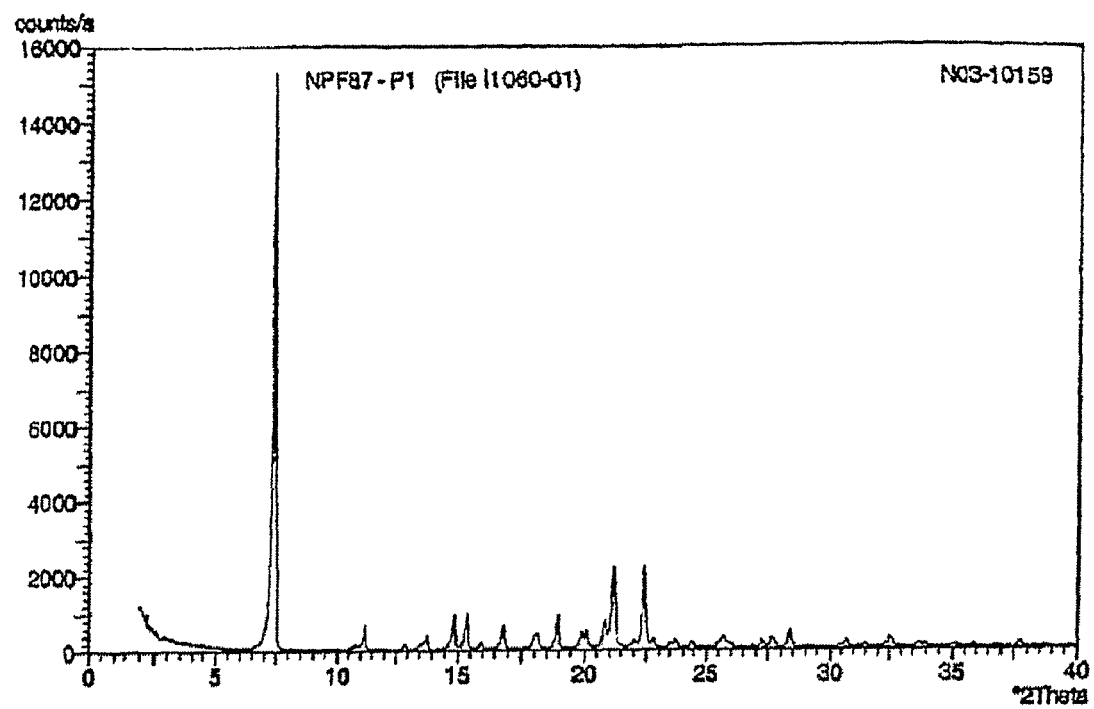
Figure 1B:
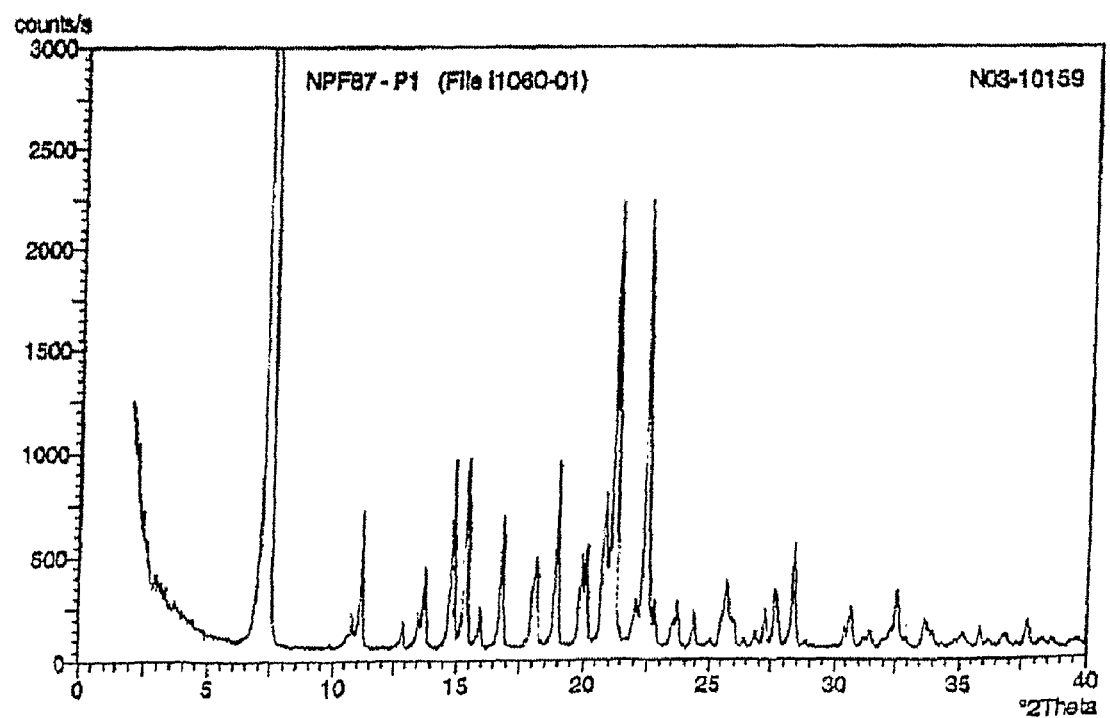

Polymorph B preferably exhibits the following signal positions (in ppm) in the solid state $^{13}$C-NMR spectrum: 25.1, 29.0, 30.5, 41.6, 44.1, 58.1, 115.2, 117.6, 123.4, 124.3, 127.3, 128.0, 129.5, 132.7, 133.9, 136.4, 137.3, 180.0.

The signal positions (in ppm) in particular at 180.0, 136.4, 127.3, 117.6, 58.1, 44.1, 41.6 in the $^{13}$C-CPMAS spectrum are typical of polymorph B.

In order to indicate the difference from polymorph A, characteristic peaks in the solid state $^{13}$C-NMR spectra of polymorphs A and B are compared in Table 1 below.

TABLE 1

Solid state $^{13}$C-NMR signal positions.

| Polymorph A | Polymorph B |
|---|---|
| *19.5 | *18.3 |
| *25.0 | — |
| 26.4 | 25.1 |
| — | *27.9 |
| 28.9 | 29.0 |
| 29.4 | 30.5 |
| *30.3 | *34.4 |
| *31.8 | *37.0 |
| *33.5 | *37.9 |
| *35.3 | — |
| *37.7 | — |
| 42.7 | 41.6 |
| — | 44.1 |
| 57.6 | 58.1 |
| 115.2 | 115.2 |
| 118.9 | 117.6 |
| 123.1 | 123.4 |
| 124.4 | 124.3 |
| — | 127.3 |
| 128.5 | 128.0 |
| 129.7 | 129.5 |
| 131.2 | — |
| 132.9 | 132.7 |
| 134.7 | 133.9 |
| 135.3 | 136.4 |
| 137.0 | 137.3 |
| 178.8 | 180.0 |

Side-band signals (spinning side bands) are identified by an asterisk (*) (artefacts of the CPMAS measuring technique). They cannot be used for polymorph assignment.

Polymorph B can also be characterized by the X-ray diffraction diagram (powder diffractogram). It has the following characteristic 2θ values, determined with a STOE powder diffraction system powder diffractometer from Stoe, Darmstadt, using monochromatic CuKα1 radiation, of 8.2, 9.7, 12.8, 18.8 and 19.3. Polymorph B preferably has the X-ray diffraction diagram shown in FIGS. 2a and 2b.

Table 2 below compares the powder diffractometric data for polymorphs A and B.

TABLE 2

Comparison of the powder diffractometric data (2-theta and lattice spacings d) for the two polymorphs A and B

| Polymorph A | | | Polymorph B | | |
|---|---|---|---|---|---|
| 2θ | d | relative Intensity | 2θ | d | relative Intensity |
| 7.5 | 11.9 | 100.00 | | | |
| | | | 8.2 | 10.8 | 60.0 |
| | | | 9.7 | 9.1 | 70.4 |
| 10.8 | 8.2 | 8.3 | | | |
| 11.2 | 7.9 | 18.6 | | | |
| | | | 12.8 | 6.9 | 40.6 |
| 13.8 | 6.4 | 12.6 | | | |
| 14.9 | 5.9 | 12.7 | | | |
| 15.4 | 5.8 | 24.2 | | | |
| 15.9 | 5.6 | 10.0 | | | |
| 16.8 | 5.3 | 23.4 | 16.7 | 5.3 | 51.0 |
| 18.1 | 5.0 | 20.1 | 17.4 | 5.1 | 26.9 |
| 18.2 | 4.9 | 20.1 | | | |
| 19.0 | 4.7 | 27.4 | 18.8 | 4.7 | 100.0 |
| 19.9 | 4.5 | 16.8 | 19.3 | 4.6 | 32.0 |
| 20.1 | 4.4 | 20.2 | | | |
| | | | 20.4 | 4.4 | 8.3 |
| 20.8 | 4.3 | 30.0 | | | |
| 21.2 | 4.2 | 68.5 | 20.9 | 4.3 | 66.4 |
| | | | 21.4 | 4.15 | 24.4 |
| 22.0 | 4.1 | 10.8 | 21.8 | 4.1 | 38.6 |
| 22.4 | 4.0 | 33.3 | | | |
| 22.8 | 3.9 | 12.5 | 22.9 | 3.9 | 22.8 |
| 23.7 | 3.7 | 11.9 | 23.4 | 3.8 | 13.9 |
| 24.4 | 3.6 | 7.7 | | | |
| 25.7 | 3.5 | 14.8 | | | |
| 26.4 | 3.4 | 6.0 | 25.8 | 3.4 | 15.6 |
| 27.2 | 3.3 | 11.8 | 27.9 | 3.2 | 8.2 |
| 27.7 | 3.2 | 17.0 | 27.2 | 3.3 | 14.8 |
| 28.4 | 3.1 | 20.2 | | | |
| 30.4 | 3.0 | 7.8 | 29.4 | 3.0 | 16.9 |
| 30.7 | 2.9 | 9.4 | 30.5 | 2.9 | 10.7 |
| 31.2 | 2.9 | 5.1 | 30.9 | 2.9 | 11.0 |
| 32.3 | 2.8 | 8.6 | | | |
| 32.5 | 2.7 | 10.2 | | | |
| 33.7 | 2.7 | 9.0 | 33.3 | 2.7 | 8.7 |
| 33.9 | 2.6 | 7.0 | | | |
| | | | 38.8 | 2.3 | 5.5 |

Polymorph B has a narrow particle size distribution: $d_{10}$-$d_{90}$=1.8 μm-15.9 μm. The average particle size is 6.7 μm. Particle size measurements were carried out by means of laser diffraction spectra using the Helios-Sympatec system: dry disperser RODOS; focal length 50 mm.

Some characteristic properties of polymorph B are compiled, comparing with polymorph A, in Table 3 below:

TABLE 3

| Characteristic parameters | | Polymorph A | Polymorph B |
|---|---|---|---|
| Solid state $^{13}$C-NMR (ppm) | | 179.2-179.5 | 180.5-180.9 |
| X-ray diffraction diagram (d, 2H) | | 7.36 | 8.41 |
| Particle size distribution | | 2-500 μm | 0.5-70 μm |
| Average particle size | | | 6.7 μm |
| Crystal morphology | | rhombi | needles |
| Crystal system | | monoclinic | monoclinic |
| Space group | | P 21/n | P 21/c |
| Unit cell: | | | |
| Length (A) | a | 14.018 | 10.482 |
| | b | 10.543 | 17.727 |
| | c | 14.710 | 10.966 |
| Angle | α | 90.0 | 90.0 |
| (degree) | β | 111.5 | 90.7 |
| | γ | 90.0 | 90.0 |

Polymorph B has a crystalline structure and high purity. Owing to the crystalline structure, polymorph B is stable during drying and storage. No phase transitions and no secondary aggregations are to be observed.

Polymorph B exhibits a compact crystalline structure with a relatively small surface area. Surface phenomena such as electrostatic charging, adhesion, adsorption etc. occur to a distinctly smaller extent by comparison with polymorph A. The crystal structure additionally results in a high chemical stability. Owing to the narrow particle size distribution compared with polymorph A, it is possible to employ polymorph B directly for producing pharmaceutical formulations. An additional grinding step is unnecessary.

The preparation of polymorph B starts from the hemisolvate of ML 3000 with an aromatic hydrocarbon. Suitable as aromatic hydrocarbon are in particular xylene (as mixture of isomers or in the form of the individual isomers) and preferably toluene. Polymorph B is obtained from the hemisolvate with the aromatic hydrocarbon by treatment at elevated temperature, in particular at a temperature in the range from 30° C. to 80° C., preferably 35° C. to 70° C. The duration of the treatment at elevated temperature depends on the temperature employed. In general, the treatment time is in the range from 3 hours to 4 days. The treatment of the hemisolvate preferably takes place under reduced pressure, which is generally in the range from 1 mbar to 500 mbar, in particular 5 mbar to 200 mbar.

The hemisolvate of ML 3000 with an aromatic hydrocarbon is prepared starting from a solution of ML 3000 in a suitable organic solvent. Suitable solvents are in particular ethers such as diethyl ether, methyl tertiary butyl ether, tetrahydrofuran or dioxane, and esters such as ethyl acetate. The hemisolvate is then obtained from the solution by adding the aromatic hydrocarbon. It is possible in this connection to carry out a precipitation of the hemisolvate by adding an excess of the aromatic hydrocarbon. Alternatively, a smaller amount of aromatic hydrocarbon can be added, so that the hemisolvate crystallizes out of a mixture of the aromatic hydrocarbon with the solvent used to dissolve ML 3000. If desired, part of the solvent can be distilled out before and/or after addition of the aromatic hydrocarbon. The crystallization of the hemisolvate preferably takes place at a temperature in the range from 0 to 10° C.

For example, ML 3000 forms with toluene a hemisolvate which shows in DSC (differential scanning calorimetry) a desolvation in the temperature range above 90° C. with a temperature maximum at 95-97° C. A further endotherm is located in the range 160-175° C.

The preparation of 6-(4-chlorophenyl)-2,2-dimethyl-7-phenyl-2,3-dihydro-1H-pyrrolizin-5-ylacetic acid (ML 3000) expediently takes place starting from the compound of the formula IV as shown in the following reaction diagram:

The process is explained in detail in WO 01/55149. The contents of WO 01/55149 are incorporated herein by reference. Further possibilities for the preparation are described in the prior art cited at the outset, which is likewise incorporated herein by reference.

The inventive compound (polymorph B) has proved to be a potent cyclooxygenase and/or lipoxygenase inhibitor. It is notable for a strong analgesic effect and for a similar inhibitory effect on the enzymes cyclooxygenase (CO) and lipoxygenase (LO) ($IC_{50}LO/IC_{50}CO\sim 1$). It can therefore be used in the treatment of disorders associated with a change in arachidonic acid metabolism. Particular mention should be made of rheumatoid diseases and the prevention of allergy-induced disorders. The inventive compound thus represents an effective anti-inflammatory, analgesic, antipyretic and antiallergic agent and has antibronchoconstrictor activity and can additionally be used for the prophylaxis of thrombosis and the prophylaxis of anaphylactic and septic shock and for the treatment of dermatological disorders such as psoriasis, urticaria, acute and chronic exanthemas of allergic and nonallergic origin. In addition, it can be used for the treatment of hypercholesterolaemia.

The inventive compound can be administered either as single therapeutic active ingredient or as mixture with other therapeutic active ingredients. It can be administered as such, but it is generally administered in the form of a pharmaceutical composition, i.e. as a mixture of the active ingredient with pharmaceutically acceptable excipients, especially carriers or diluents and/or additives. The compound or the composition can be administered enterally, e.g. orally or rectally, or parenterally, e.g. subcutaneously, intravenously or intramuscularly, but they are preferably given in oral dosage forms.

The nature of the pharmaceutical composition and of the pharmaceutical carrier or diluent depends on the desired mode of administration. Oral compositions can be in the form for example of tablets or capsules and may comprise conven-

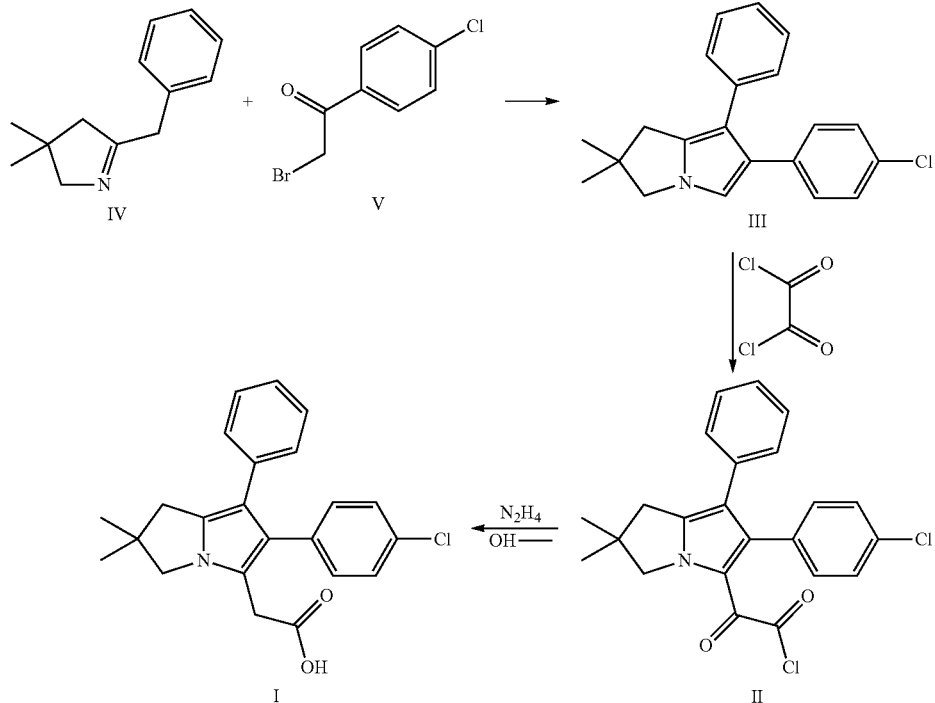

tional excipients such as binders (e g. syrup, acacia, gelatin, sorbitol, tragacanth or polyvinylpyrrolidone), fillers (e.g. lactose, sugar, maize starch, calcium phosphate, sorbitol or glycine), lubricants (e.g. magnesium stearate, talc, polyethylene glycol or silicon dioxide), disintegrants (e.g. starch) or wetting agents (e.g. sodium lauryl sulphate). Oral liquid products can be in the form of aqueous or oily suspensions, solutions, emulsions, syrups, elixirs or sprays etc. or may be in the form of dry powders for reconstitution with water or another suitable carrier. Such liquid products may comprise conventional additives, for example suspending agents, flavourings, diluents or emulsifiers. Solutions or suspensions with conventional pharmaceutical carriers can be employed for parenteral administration.

Treatment with the inventive compound takes place by administering an effective amount of the compound, usually formulated in accordance with pharmaceutical practice, to the individual to be treated, preferably a mammal, in particular a human. Whether such a treatment is indicated and the form in which it is to take place depends on the individual case and is subject to a medical assessment (diagnosis) which takes account of the signs, symptoms and/or dysfunctions present, and of the risks of developing particular signs, symptoms and/or dysfunctions, and further factors.

Treatment usually takes place by a single or multiple daily administration where appropriate together with or alternately with other active ingredients or active ingredient-containing products, so that a daily dose of about 10 mg to about 2000 mg and in particular 10 mg to about 1000 mg is supplied to the individual to be treated.

The following examples illustrate the invention without limiting it.

EXAMPLE 1

6-(4-Chlorophenyl)-2,2-dimethyl-7-phenyl-2,3-dihydro-1H-pyrrolizine 4.64 kg (190.9 mol) of magnesium and 18.8 kg of diethyl ether are introduced successively into a 250 l reactor after evacuation and introduction of $N_2$ three times. The ether is brought to reflux. With the stirrer switched off, 0.03 kg of iodine and 0.5 kg (4 mol) of benzyl chloride are added, whereupon the reaction of the magnesium with the halide starts immediately (decoloration and turbidity). With the stirrer switched on, a solution of 23.5 kg (185.6 mol) of benzyl chloride in 37.8 kg of diethyl ether is added from an addition vessel over the course of 2 h, during which the blackish-grey mixture refluxes strongly. After the addition is complete, the Grignard solution is kept at reflux for a further 2 h. Then, at the reflux temperature, a solution of 17.7 kg (134.6 mol) of distilled 4-chloro-3,3-dimethylbutyronitrile in 48.5 kg of diethyl ether are added from the addition vessel over the course of 1.5 h. The reaction mixture is heated to reflux for a further 2 h. The diethyl ether is then distilled out of the pale grey suspension under atmospheric pressure. 54-59 kg of distillate are removed (time taken 2 h) so that the reaction mixture remains stirrable.

106.3 kg of toluene are added to the residue. The internal temperature is 43° C. An ether/toluene mixture is then distilled out until an internal temperature of 85-90° C. is reached (about 36-40 kg of distillate).

The residue becomes a thick, but still stirrable, suspension without crust. This suspension is transferred into a reactor into which 76.7 kg of ice and 38.5 kg of 32% strength hydrochloric acid had previously been introduced. During the introduction, the internal temperature of the phases rises from 0 to 23° C. The pH of the aqueous phase should be between 0.5 and 1.5 (pH=1.0). After the reactor has been heated to an internal temperature of 40-45° C., the phases are vigorously mixed by stirring for 1.75-2 h. Phase separation is then effected by leaving to stand at this temperature and with the stirrer switched off for 10-15 min. The aqueous phase containing the product is separated off (147 kg).

The aqueous phase is cooled in an extraction apparatus to −8 to 0° C. and then made alkaline with 33.2 kg of 24% strength ammonia, controlling the rate of addition of the ammonia so that the internal temperature does not exceed a maximum of 5° C. The pH is 10.5-11.

The alkaline aqueous phase is thoroughly mixed with 106.3 kg of diethyl ether by stirring at 10-25° C. for 30-40 min, and then left to stand for 25-30 min for phase separation. The clear, pale yellow aqueous phase (170 kg) is separated off and discarded. The clear, yellowish green ether phase is completely concentrated in vacuo (0.7-0.8 mbar), obtaining 95 kg of ether distillate (1.40 h). The residue resulting from the distillation is 20.6 kg of pale green oil which comprises 86.7% of 2-benzyl-4,4-dimethyl-1-pyrroline. 20.6 kg of the residue (86.7% pure), equivalent to 17.9 kg (95.5 mol) of 2-benzyl-4,4-dimethyl-1-pyrroline, 29.7 kg (127.2 mol, 1.33 equiv.) of ω-bromo-4-chloroacetophenone and 226.6 kg of methanol are introduced into a reactor (500 l). Addition of 12.7 kg (151.2 mol, 1.58 equiv.) of sodium bicarbonate is followed by stirring with exclusion of light at 17-24° C. to form a beige suspension. The reaction is continued until the content of pyrroline compound remaining in the mixture is <5%. After 17 h, a sample is taken and examined by gas chromatography for the content of pyrroline compound. Analysis revealed a content of 2%. The suspension is then centrifuged at an internal temperature of 18-22° C., and the solid obtained by centrifugation is washed with 14.4 kg of methanol in 2 portions. The still moist, pale yellow powder weighs 25.8 kg.

The still moist crude product (25.8 kg) is suspended in 150 kg of water and then heated to an internal temperature of 50-60° C. over the course of 15 min and stirred at this temperature for 40 min. The suspension which has been cooled to 40° C. (40 min) is centrifuged, and the pale yellow crystalline solid obtained by centrifugation is washed with 27 kg of water in 2 portions. The product is dried in vacuo at 50-60° C. for 12-24 h. 18.6 kg of 6-(4-chlorophenyl)-2,2-dimethyl-7-phenyl-2,3-dihydro-1H-pyrrolizine with an ash content of 0.33% and a content of the 5-(4-chlorophenyl)-2,2-dimethyl-7-phenyl-2,3-dihydro-1H-pyrrolizine isomer of 1.0% are obtained.

EXAMPLE 2

Preparation of 6-(4-chlorophenyl)-2,2-dimethyl-7-phenyl-2,3-dihydro-1H-pyrrolizin-5-ylacetic acid·½ toluene 6-(4-Chlorophenyl)-2,2-dimethyl-7-phenyl-2,3-dihydro-1H-pyrrolizin-5-ylacetic acid (4 g) is dissolved under reflux (60° C.) in a solvent mixture composed of diethyl ether and toluene in the ratio 1:1 (40 ml). A saturated solution with a pale yellow colour is obtained and is rapidly filtered while still hot under pressure and is then slowly cooled while stirring with a reflux condenser by immersion in an oil bath equilibrated at 35° C. and finally with the stirring switched off to room temperature over the course of 6 h. It is then stored in a refrigerator at 4° C. for 16 hours. The crystals are removed by filtration of the mother liquor through a G4 filter under a nitrogen pressure and adhering residues of mother liquor are removed by passing air through the bed of powder for 10 minutes. The toluene solvate is obtained in the form of fine white crystals in a yield of 70% and purity of 99.83%.

EXAMPLE 3

Preparation of polymorph B of 6-(4-chlorophenyl)-2,2-dimethyl-7-phenyl-2,3-dihydro-1H-pyrrolizin-5-ylacetic acid by crystallization from ethyl acetate/toluene 30 l of ethyl acetate are distilled out of a solution of crude 6-(4-chlorophenyl)-2,2-dimethyl-7-phenyl-2,3-dihydro-1H-pyrrolizin-5-ylacetic acid (12 kg) in ethyl acetate (125 l) at 40-50° C. under reduced pressure and are replaced by 30 l of toluene. Subsequently, a further 30 l of ethyl acetate are distilled out of the mixture in vacuo. The crystals which form during this are removed by centrifugation, washed with toluene (2 l), resuspended in toluene (11 l) and again centrifuged. After washing with toluene (1 l), the crystals (toluene solvate) from a number of batches are collected, suspended in ethyl acetate (45 l) under nitrogen and stirred at 0-5° C. for 2 hours, and subsequently centrifuged. The centrifugate is washed with ethyl acetate (2×8 l) and resuspended in methanol (60 l) at 0-5° C. for 3 hours, and finally centrifuged, and the centrifugate is washed with methanol (4 l) and the product is dried in vacuo at 20 mbar and 50° C. for 2 days. Polymorph B of 6-(4-chlorophenyl)-2,2-dimethyl-7-phenyl-2,3-dihydro-1H-pyrrolizin-5-ylacetic acid is obtained in a purity of 99.69%.

Figure 2A:
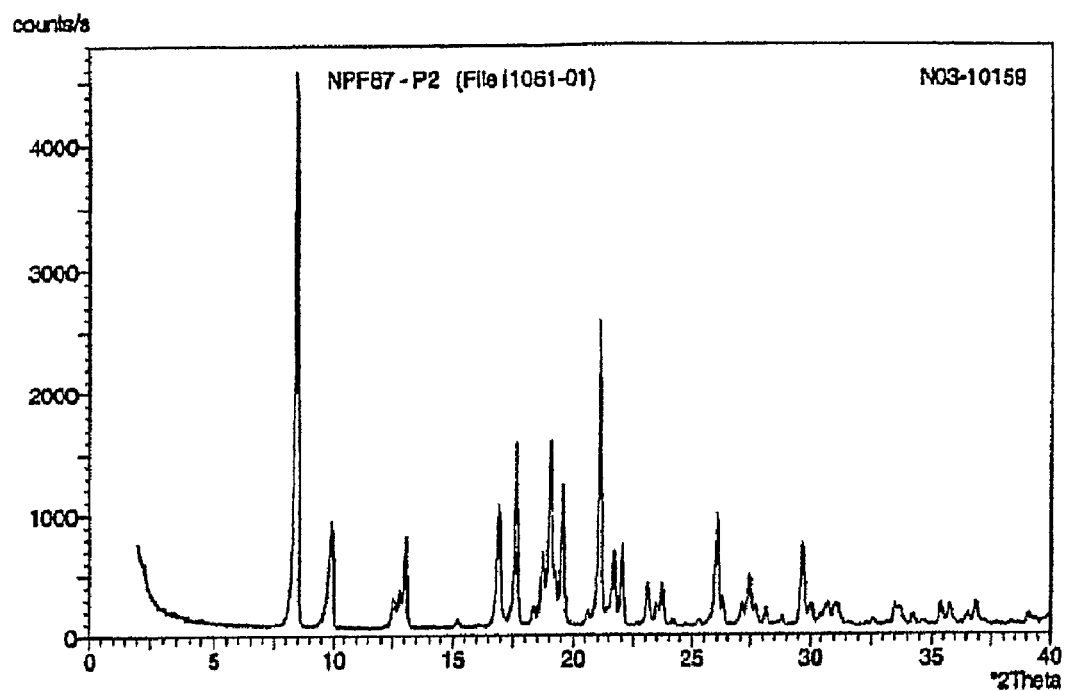
Figure 2B:
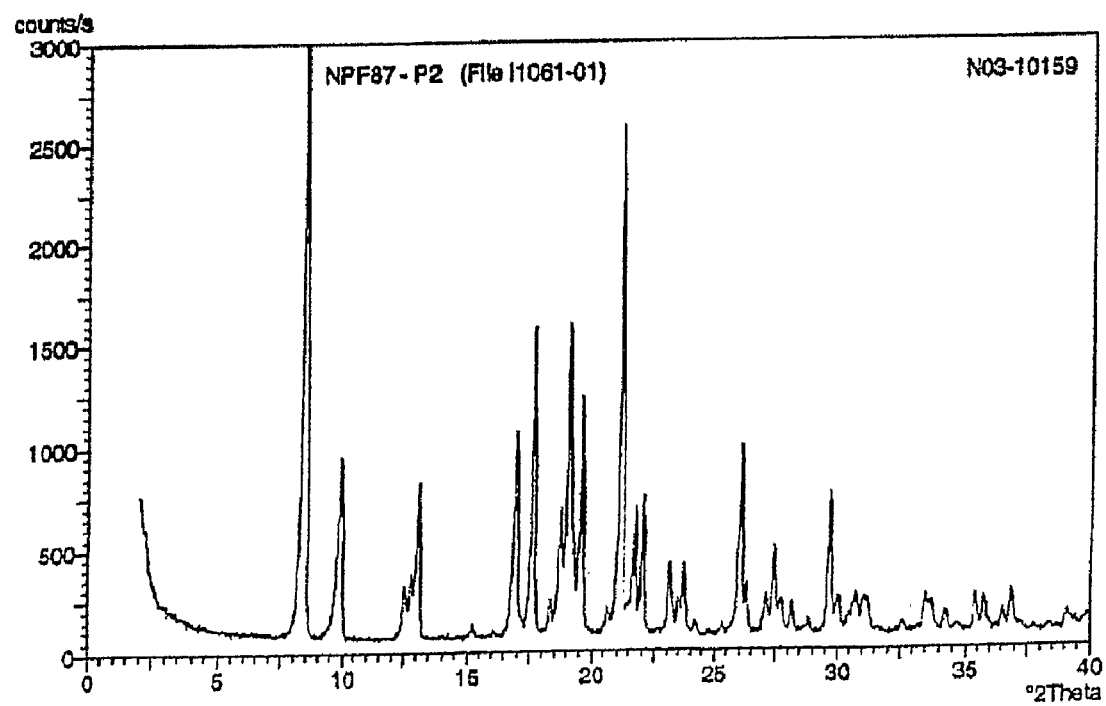
Figure 3:
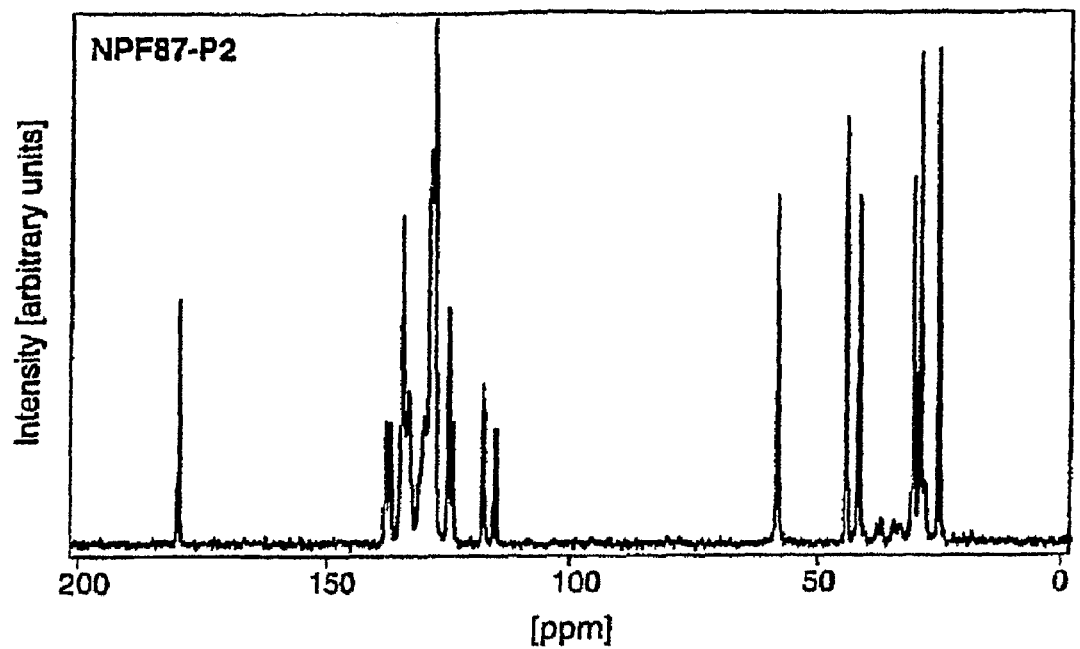
Figure 4:
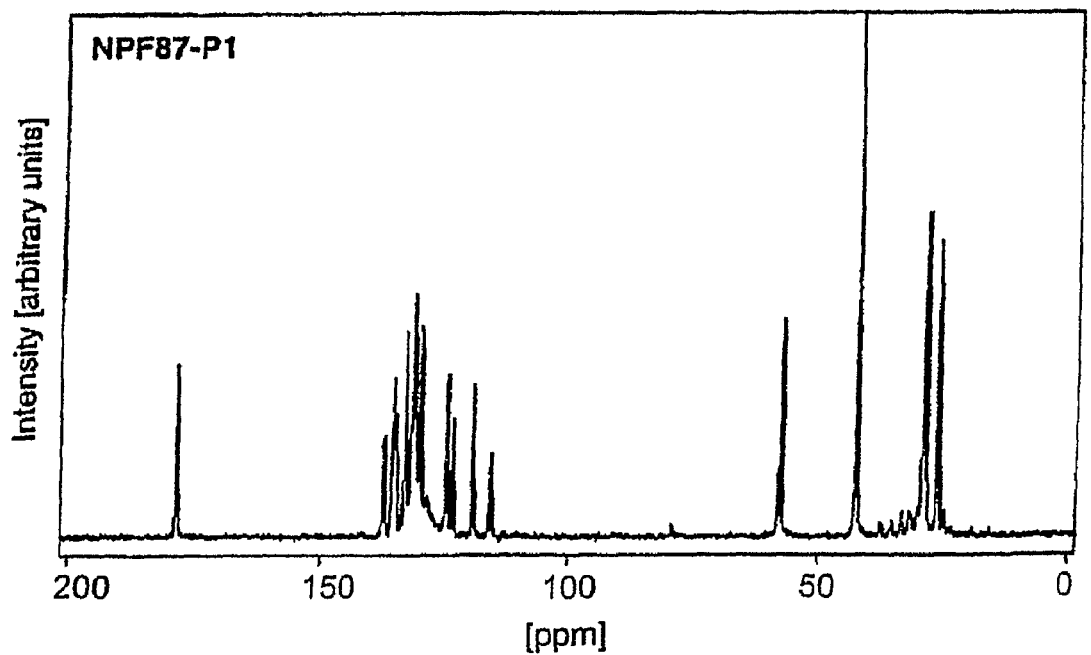

Solid state $^{13}$C-NMR spectrum and X-ray diffraction diagram are shown in FIGS. 2a and 2b, and 3, respectively.

The invention claimed is:

1. Polymorphic form B of 6-(4-chlorophenyl)-2,2-dimethyl-7-phenyl-2,3-dihydro-1H-pyrrolizin-5-ylacetic acid of the formula

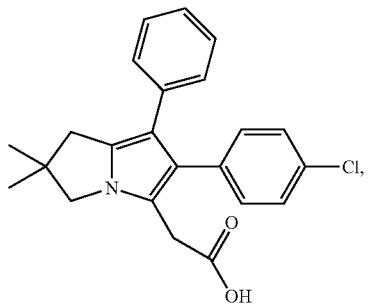

having the following peaks, in ppm, in the solid state $^{13}$C-NMR spectrum, with adamantane as external reference standard; CH group δ=29.45 ppm: 25.1, 29.0, 30.5, 41.6, 44.1, 58.1, 115.2, 117.6, 123.4, 124.3, 127.3, 128.0, 129.5, 132.7, 133.9, 136.4, 137.3, 180.0.

2. A pharmaceutical composition comprising the polymorphic form according to claim 1, together with a pharmaceutically acceptable excipient.

3. A method for the treatment of rheumatoid diseases which comprises administering to a person in need of such treatment a therapeutically effective amount of polymorphic form B of 6-(4-chlorophenyl)-2,2-dimethyl-7-phenyl-2,3-dihydro-1H-pyrrolizin-5-ylacetic acid according to claim 1.

4. Polymorphic form B of 6-(4-chlorophenyl)-2,2-dimethyl-7-phenyl-2,3-dihydro-1H-pyrrolizin-5-ylacetic acid of the formula

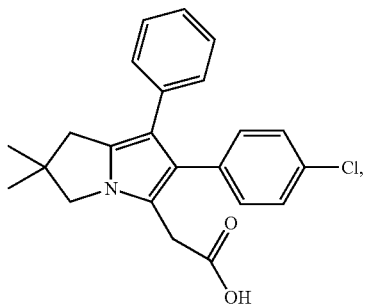

having the following characteristic peaks in the X-ray diffraction diagram (2θ values): 8.2, 9.7, 12.8, 18.8 and 19.3.

5. The polymorphic form B of 6-(4-chlorophenyl)-2,2-dimethyl-7-phenyl-2,3-dihydro-1H-pyrrolizin-5-ylacetic acid according to claim 1, wherein the polymorphic form B has the following characteristic peaks in the X-ray diffraction diagram (2θ values): 8.2, 9.7, 12.8, 18.8 and 19.3.

6. A pharmaceutical composition comprising the polymorphic form according to claim 4, together with a pharmaceutically acceptable excipient.

7. A method for the treatment of rheumatoid diseases which comprises administering to a person in need of such treatment a therapeutically effective amount of polymorphic form B of 6-(4-chlorophenyl)-2,2-dimethyl-7-phenyl-2,3-dihydro-1H-pyrrolizin-5-ylacetic acid according to claim 4.

* * * * *